US012788820B2

(12) United States Patent
Wang et al.

(10) Patent No.: US 12,788,820 B2
(45) Date of Patent: Nov. 10, 2026

(54) METHOD OF PREPARING PEGYLATED BIOMOLECULES HAVING CONTROLLABLE BINDING SITES

(71) Applicant: JENKEM TECHNOLOGY CO., LTD. (TIANJIN), Tianjin (CN)

(72) Inventors: Qingbin Wang, Tianjin (CN); Jie Qi, Tianjin (CN); Yu Li, Tianjin (CN); Xuan Zhao, Tianjin (CN)

(73) Assignee: JENKEM TECHNOLOGY CO., LTD. (TIANJIN), Tianjin (CN)

( * ) Notice: Subject to any disclaimer, the term of this patent is extended or adjusted under 35 U.S.C. 154(b) by 1355 days.

(21) Appl. No.: 17/418,671

(22) PCT Filed: Dec. 27, 2019

(86) PCT No.: PCT/CN2019/129052
§ 371 (c)(1),
(2) Date: Jun. 25, 2021

(87) PCT Pub. No.: WO2020/135683
PCT Pub. Date: Jul. 2, 2020

(65) Prior Publication Data

US 2022/0125939 A1 Apr. 28, 2022

(30) Foreign Application Priority Data

Dec. 27, 2018 (CN) ........................ 201811607603.2

(51) Int. Cl.

| | |
|---|---|
| ***A61K 47/60*** | (2017.01) |
| ***A61K 38/20*** | (2006.01) |
| ***A61P 31/04*** | (2006.01) |
| ***A61P 31/12*** | (2006.01) |
| ***A61P 35/00*** | (2006.01) |
| ***A61P 37/02*** | (2006.01) |
| ***C08G 65/32*** | (2006.01) |

(52) U.S. Cl.
CPC .......... *A61K 47/60* (2017.08); *A61K 38/2013* (2013.01); *A61P 31/04* (2018.01); *A61P 31/12* (2018.01); *A61P 35/00* (2018.01); *A61P 37/02* (2018.01); *C08G 65/32* (2013.01)

(58) Field of Classification Search
CPC .... A61K 47/60; A61K 38/2013; C08G 65/32; C07K 14/7155; C07K 14/55
See application file for complete search history.

(56) References Cited

FOREIGN PATENT DOCUMENTS

| | | | |
|---|---|---|---|
| WO | WO 1998/40409 | * 9/1998 | C07K 17/02 |
| WO | WO 2007/139997 | * 12/2007 | C07K 14/47 |

OTHER PUBLICATIONS

Katre NV, Knauf MJ, Laird WJ. Chemical modification of recombinant interleukin 2 by polyethylene glycol increases its potency in the murine Meth A sarcoma model. Proc Natl Acad Sci U S A. Mar. 1987;84(6):1487-91. doi: 10.1073/pnas.84.6.1487. PMID: 3494243; PMCID: PMC304459. (Year: 1987).*
Snyder LR. Chromatogr Rev. 1965;7:1-51. (Year: 1965).*
Tsui et al. Cancer Cell Int. Apr. 17, 2009;9:9. (Year: 2009).*
Stauber et al. Proc Natl Acad Sci U S A. Feb. 21, 2006;103(8):2788-93. (Year: 2006).*
Mao et al. Molecular Simulation, 44(12), 973-980. Published Online Apr. 27, 2018. (Year: 2018).*
Wang et al. Annu Rev Immunol. 2009;27:29-60. (Year: 2009).*

* cited by examiner

*Primary Examiner* — Jeffrey Stucker
*Assistant Examiner* — Sarah Cooper Patterson
(74) *Attorney, Agent, or Firm* — NIXON & VANDERHYE, PC

(57) ABSTRACT

The present invention discloses a method of preparing PEGylated biomolecules having controllable binding sites, including the following steps: (1) binding a blocker to a biomolecule; (2) PEGylating the biomolecule; and (3) separating the blocker from the biomolecule. In another aspect, the present invention discloses a method for preparing PEGylated IL-2 having controllable binding sites, including the following steps: (1) binding IL-2 to an IL-2α receptor, closing the a binding site of the IL-2; (2) PEGylating, coupling PEG with the IL-2; and (3) separating the IL-2 from the IL-2α receptor. By regulating IL-2 binding sites and a PEGylation process only adding one or two polyethylene glycols, the IL-2 is caused to selectively bind to an IL-2R βγ-type receptor.

1 Claim, 2 Drawing Sheets

METHOD OF PREPARING PEGYLATED BIOMOLECULES HAVING CONTROLLABLE BINDING SITES

RELATED APPLICATIONS

This application is a United States National Stage Application filed under 35 U.S.C 371 of PCT Patent Application Serial No. PCT/CN2019/129052, filed Dec. 27, 2019, which claims Chinese Patent Application Serial No. CN 201811607603.2, filed Dec. 27, 2018, the disclosure of all of which are hereby incorporated by reference in their entirety.

TECHNICAL FIELD

The present invention belongs to the technical field of medicine, and particularly relates to a method of preparing PEGylated biomolecules having controllable binding sites.

BACKGROUND

Interleukin-2 (IL-2) is produced when lymphoproliferation is stimulated by phytohemagglutinin (PHA) and other mitogens. Recently, more and more researches on this factor and its receptor have been carried out, and it has been found that the IL-2 plays an important role in cellular immunity, humoral immunity, and immune regulation. In particular, the role and clinical significance of immunotherapy in tumors have been emphasized by many authors.

IL-2 is produced mostly by CD4+ T helper cells (Th) and a few IL-2 is produced by CD8+ and other immune cells. These cells can secrete IL-2 under the action of IL-1. IL-2 produced by lymphocytes acts on cells with IL-2 receptors on the surface, so that the cells can proliferate to play a biological function, and can act on normal T and B lymphocytes, precursor cells of NK cells, cytotoxic T cells (CTL), precursor cells of lymphokine activated killer cells, etc. Biological functions of IL-2 include: 1. maintaining the long-term survival of activated T cells in vitro and maintaining the biological functional activity of the activated T cells, where under the action of IL-2, some T cells activated by tumor antigens can enhance the function of killing tumor cells and enhance the anti-tumor effect; 2. promoting proliferation and differentiation of B cells and generating antibodies; and 3. stimulating secretion of a granulocyte-macrophage colony stimulating factor, γ-interferon, etc., and promoting expression of these receptors in lymphocytes; maintaining the proliferation of thymus in the presence of a subdose of mitogen; and promoting the expression of the IL-2 receptor, participating in an immune regulation system of a body, and maintaining immune balance and stability.

IL-2 is an earliest immunotherapeutic agent. As early as 1992 and 1998, the U.S. FDA approved the IL-2 drug (Aldesleukin) for advanced renal cancer and malignant melanoma with an effective rate of 15-20%, and nearly 10-15% of patients may survive for over 5 years. However, due to high doses for clinical use, IL-2 has significant side effects, such as severe hypotension and vascular leak syndrome. At that time, patients treated with IL-2 must be hospitalized and observed closely around the clock, because little carelessness may cause risk of life. Therefore, the significant side effects limit the use of IL-2, which most clinicians do not dare to use with ease.

The mechanism of action of IL-2 is as follows: IL-2 is produced primarily by antigen-stimulated CD4+ T cells, and may also be secreted by CD8+ T cells, NK cells and DC cells. High doses of IL-2 can promote the differentiation of CD4+ T cells and the proliferation of CD8+ T cells and NK cells, and increase their lethality to mobilize the body's immune response. In turn, low doses of IL-2 can promote the proliferation of regulatory T cells and inhibit the immune system, so low doses of IL-2 are often used to treat autoimmune diseases.

This difference is mainly caused by the different distribution of IL-2 receptors on the surfaces of immune cells. The IL-2 receptor totally has three subunits α, β and γ. The receptor on the surfaces of killer cells such as CD8 positive T cells and NK cells mainly has subunits β and γ (IL-2R βγ). This receptor has a low affinity for IL-2 and cannot be activated until high doses of IL-2. Most antibodies on the surfaces of regulatory T cells are high affinity antibodies (IL-2R αβγ) having three subunits α, β and γ, and low doses of IL-2 may activate them more easily to play an immunosuppressive role.

While IL-2 has been approved for the treatment of renal cell tumor and metastatic melanoma more than 20 years ago, it has been abandoned and barely applied in immunotherapy. The main reasons are as follows: 1. the effective rate is low, and the effective rate of IL-2 alone can only reach about 15-20%; 2. IL-2 has a double-edged function, i.e., low doses of IL-2 promotes the proliferation of regulatory T cells but causes immunosuppression, and how to regulate the double-edged function is still to be solved; 3. the half-life is short, i.e., only a few minutes, and large doses must be administered in order to continuously take effect; and 4. adverse reactions are severe, an over-activated immune system may possibly attack self-organs to cause organ failure, and the dosage window is narrow. In order to improve the efficacy of IL-2 and reduce adverse reactions, scientists have also tried various combined solutions, e.g., IL-2+ interferon, IL-2+ lymphokine activated killer (LAK) cell therapy and IL-2+ chemotherapy, which all have an unideal effect.

In recent years, scientists have found: by adding chemical modifications to normal IL-2 molecules, the effect of IL-2 can be maintained, meanwhile the use concentration is reduced, and the side effects are also reduced. Consequently, NKTR-214 was born. NKTR-214 is not mysterious and is essentially an upgraded version of the old drug IL-2 that was marketed more than 20 years ago, but it has lower side effects and higher specificity (higher ease to activate CD8 rather than Treg cells), and may more efficiently activate the immune system. Specifically, six polyethylene glycols (PEGs) are added to an IL-2 molecule for modification to form an inactive drug. Surprisingly, after injection into tumor patients, these six PEG modifications gradually shed, forming active forms of 2-PEG and 1-PEG.

NKTR-214 is PEGylated IL-2 and the activity of the original drug is very low. Six PEG chains were cleverly ligated to sites where the subunit α of IL-2R αβγ high affinity antibodies can bind in IL-2, making PEGylated IL-2 more likely to bind to IL-2R βγ-type receptors in killer immune cells. As the PEGs are degraded one by one, the activity of the drug is released slowly. NKTR-214 addresses two major pain points of IL-2 in tumor therapy: firstly, the effect of drug slow release is achieved through PEG degradation, so that the tolerance is greatly improved; and secondly, the selectivity to the killer immune cells is improved, so that the expression amount of the immune cells PD-1 in the microenvironment is increased.

The Nektar company announced in Nasdaq on Oct. 7, 2015 that a new drug application for NKTR-214 was filed to the U.S. Food and Drug Administration (FDA). The company has completed a preclinical study of NKTR-214 and plans to initiate phase I and phase II clinical studies of the drug by the end of 2015.

In preclinical studies, the AUC value of NKTR-214 in tumors after single dose administration was nearly 400 times that of Aldesleukin compared with an existing IL-2 therapeutic drug Aldesleukin. In addition, the data provided by the Nektar company indicates that NKTR-214 exhibited long-lasting anti-tumor immunotherapeutic effects in multiple preclinical animal models; and in a tumor infiltrating lymphocyte model, after NKTR-214 treatment, the ratio of CD8 positive T cells to CD4 positive T cells was about 450:1, showing a strong tumor killing effect. Therefore, NKTR-214 is an immune stimulator anti-cancer drug, has a therapeutic effect similar to that of an antibody, and can stimulate the growth of T cells, so as to realize a tumor killing effect. Preclinical experimental results show that the drug has a long-acting anti-tumor therapeutic effect, and is an extremely promising anti-cancer drug.

However, during actual production, 6 PEGs were added to a normal IL-2 molecule by chemical modification to form NKTR-214, so as to selectively bind IL-2 to IL-2R βγ-type receptors. In the present invention, the applicant provides a method of preparing PEGylated biomolecules having controllable binding sites. The binding sites of the biomolecules are artificially interfered in vitro, and the binding sites are kept exposed and not PEGylated, so that the biomolecules are more targeted in vivo, and the therapeutic effect is more rapid. Specifically, when IL-2 is modified, IL-2 is caused to selectively bind to an IL-2R βγ-type receptor by regulating the IL-2 binding sites and PEGylation only adding 1 or 2 PEGs.

SUMMARY

An objective of the present invention is to provide a method of preparing PEGylated biomolecules having controllable binding sites, and in particular, the present invention provides a method for preparing PEGylated IL-2 having controllable binding sites.

The objective of the present invention is achieved by the technical solutions as below:

A method of preparing PEGylated biomolecules having controllable binding sites includes the following steps:

(1) binding a blocker to at least one binding site in a biomolecule;

(2) PEGylating the biomolecule; and (3) separating the blocker from the biomolecule.

The biomolecule in the step (1) is selected from large biomolecules or small biomolecules having specific binding to the blocker, and the biomolecule has at least one binding site for the blocker. The blocker and the biomolecule are selected from the following combinations: a ligand and a receptor, DNA and complementary DNA or RNA thereof, an enzyme and a substrate thereof, an enzyme and a competitive inhibitor thereof, an enzyme and a co-enzyme factor thereof, vitamin and a specific binding protein thereof, and glycoprotein and corresponding lectin thereof. Preferably, the ligand and the receptor are selected from: hormone and a receptor, and a drug and a receptor.

The DNA and the complementary DNA or RNA thereof are selected from: a gene probe and a base-complementary gene sequence.

The enzyme and the substrate thereof are selected from: protease and protein, amylase and starch, nuclease and nucleic acid, lactate dehydrogenase and lactic acid, and oxaloacetic decarboxylase and oxaloacetic acid.

The enzyme and the competitive inhibitor thereof are selected from: succinate dehydrogenase and malonic acid, dihydrofolate synthetase and sulfonamides, cholinesterase and an organophosphorus pesticide, and a sulfhydryl enzyme and lewisite.

The enzyme and the co-enzyme factor thereof are selected from: pyruvate dehydrogenase and $Mn2^+$, catalase, and oxidoreductase and $Fe2^+/Fe3^+$.

The hormone and the receptor are selected from: oestrogen and an oestrogen receptor, androgen and an androgen receptor, mineralocorticoid and a mineralocorticoid receptor, thyroid hormone and a thyroid hormone receptor, and progesterone and a progesterone receptor.

The drug and the receptor are selected from: insulin, an insulin-like growth factor, an epidermal growth factor, a platelet-derived growth factor, and lymphokine, and a receptor having a tyrosine kinase activity, and epinephrine, dopamine, 5-hydroxytryptamine, M-acetylcholine, opiates, purines, prostaglandin, and polypeptide hormone drugs, and a G protein-coupled receptor.

Preferably, the drug and the receptor are selected from: folic acid and a folate receptor, and interleukin and an interleukin receptor.

More preferably, the drug and the receptor are selected from: interleukin-2 and an interleukin-2 receptor. In particular, the interleukin-2 receptor includes an interleukin-2α receptor, an interleukin-2β receptor and an interleukin-2γ receptor.

The vitamin and the specific binding protein thereof are selected from: vitamin A and a retinol binding protein, vitamin D and a vitamin D binding protein, α-tocopherol and an α-tocopherol transport protein, and vitamin K and lipoprotein.

The glycoprotein and the corresponding lectin thereof are selected from: horseradish peroxidase and concanavalin A, *Lens culinaris* agglutinin and *Pisum sativum* agglutinin, jacalin and galactose, an amaranthus lectin and N-acetylgalactosamine, a dimer chitin binding lectin and N-acetylglucosamine oligosaccharide, dolichos bifows agglutinin and a blood group substance A, and *Ulex europaeus* agglutinin and a blood group substance O (2-L-fucose).

The biomolecule PEGlyated in the step (2) has a following structure:

$$(PEG—X)_m\text{—biomolecule} \qquad (I)$$

X is a linking group between PEG and the biomolecule and is selected from: a combination of one or more of $—(CH_2)a-$, $—(CR_1R_2)a-$, $—(CH_2)aNH—$, $—NHCO(CH_2)a-$, $—(CH_2)aCONH—$, $—(CH_2)aCO—$, $—CO(CH_2)a-$, $—(CH_2)aCONH(CH_2)a-$, $—(CH_2)a\text{-}S—S—(CH_2)a-$, $—(CH_2)aCOO(CH_2)a-$ and $—(CH_2)a\text{-}S—(CH_2)a-$.

a is an integer in the range of 0-10. Preferably, the a is an integer in the range of 0-5 (e.g., 0, 1, 2, 3, 4 or 5). More preferably, the a is an integer in the range of 0-3.

m is an integer in the range of 1-12, specifically 1, 2, 3, 4, 5, 6, 7, 8, 9, 10, 11 or 12.

$R_1$ and $R_2$ are independently selected from: a combination of one or more of —H, $C_{1-6}$ alkyl, —OR', —NHR', $—N(R')_2$, —CN, —F, —Cl, —Br, —I, —COR', —COOR', —OCOR', —CONHR' or $—CON(R')_2$. Preferably, $R_1$ and $R_2$ are independently selected from: a combination of one or more of H, $C_{1-3}$ alkyl (specifically, methyl, ethyl, n-propyl or isopropyl), —OH, $C_{1-3}$ alkoxy, $—NH_2$, —F, —Cl, —Br and —I. More preferably, $R_1$ and $R_2$ are selected from: H, —$CH_3$, —OH, —$OCH_3$ and —$OCH_2CH_3$. In one embodiment of the present invention, $R_1$ is —H, and $R_2$ is selected from: —$CH_3$, —OH, —$OCH_3$ and —$OCH_2CH_3$.

R' is selected from: —H, $C_{1-6}$ alkyl, —F, —Cl, —Br or —I. Preferably, R is selected from: —H and $C_{1-3}$ alkyl (specifically, methyl, ethyl, n-propyl or isopropyl).

Preferably, the X is selected from: a combination of one or more of —$CH_2$—, —$CH_2CH_2$—, —$CH_2CH_2CH_2$—, —$CH_2CONHCH_2$—, —$CH_2CONHCH_2CH_2$—, —$CH_2CONHCH_2CH_2NH$—, —$CH_2CH_2CONHCH_2$—, —$CH_2CO$—, —$CH_2CH_2CO$—, —$CH_2CH_2CONHCH_2CH_2$—, —$CH_2NH$—, —$CH_2CONH$—, —$COCH_2$—, —$COCH_2CH_2$—, —$COCH_2CH_2CH_2$—, —$CH_2COOCH_2$— and —$CH_2$—S—$CH_2$—.

More preferably, the X is selected from: —$CH_2$—, —$CH_2CH_2$—, —$CH_2CH_2CONHCH_2$—, —$CH_2CH_2CO$— and —$CH_2COOCH_2$—.

The PEG is a linear, Y-type and multi-branch polyethylene glycol residue, for example including monomethoxy-polyethylene glycol (mPEG), linear double-terminated PEG, Y-type PEG, 4-arm branched PEG, 6-arm branched PEG or 8-arm branched PEG, etc.

Preferably, a molecular weight of the PEG is in the range of 1-100 KDa, e.g., 1-10 KDa (specifically, 1, 2, 3, 4, 5, 6, 7, 8, 9 or 10 KDa), 10-50 KDa (specifically, 10, 15, 20, 25, 30, 35, 40, 45 or 50 KDa) or 50-100 KDa (specifically, 50, 55, 60, 65, 70, 75, 80, 85, 90, 95 or 100 KDa), etc. Further preferably, the molecular weight of the PEG is in the range of 10-50 KDa.

In a specific implementation of the present invention, the PEG is a linear polyethylene glycol residue and has a structure as shown in a general formula II or III:

(II)

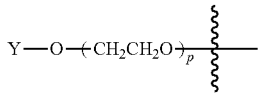

(III)

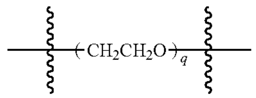

wherein p and q are independently selected from integers in the range of 1-2280, and preferably selected from integers in the range of 220-1140, Y is a capping group and is selected from: H, $C_{1-6}$ alkyl (specifically, methyl, ethyl, n-propyl, isopropyl, n-butyl, isobutyl, tert-butyl, n-pentyl, n-hexyl, etc.), $C_{3-6}$ cycloalkyl (specifically, cyclopropyl, cyclobutyl, cyclopentyl, cyclohexyl, etc.), $C_{6-10}$ aryl (specifically, phenyl, naphthyl, etc.) and -L-T, L is a linking group between oxygen (O) and a terminal group T and is selected from: a combination of one or more of —$(CH_2)_b$—, —$(CR_3R_4)_b$—, —$(CH_2)_bNH$—, —$NHCO(CH_2)_b$—, —$(CH_2)_bCONH$— and —$CO(CH_2)_b$—, and b is an integer in the range of 0-10.

$R_3$ and $R_4$ are independently selected from: a combination of one or more of —H, $C_{1-6}$ alkyl, —OR", —NHR", —$N(R")_2$, —CN, —F, —Cl, —Br, —I, —COR', —COOR", —OCOR", —CONHR" and —$CON(R")_2$.

R" is selected from: —H, $C_{1-6}$ alkyl, —F, —Cl, —Br and —I.

Preferably, L is selected from: a combination of one or more of —$CH_2$—, —$CH_2CH_2$—, —$CH_2CH_2CH_2$—, —CONH—, —NH—, —CO—, —$CONHCH_2$—, —$CH_2NH$—, —$CH_2CONH$— and —$COCH_2$—.

T is a terminal group and is selected from: H, $C_{1-6}$ alkyl, $C_{3-6}$ cycloalkyl, $C_{6-10}$ aryl, monosaccharide (specifically, glucose, fructose, galactose, ribose, deoxyribose, etc.), and oligosaccharide (specifically, residues of disaccharides including sucrose, lactose, etc. and trisaccharides including gentianose, raffinose, etc.).

Preferably, the T is selected from: methyl, ethyl, isopropyl, cyclopropyl, cyclobutyl, cyclohexyl, benzyl,

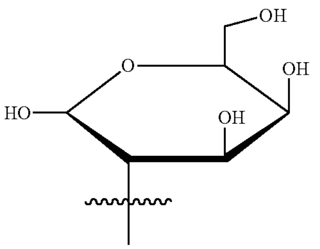

and

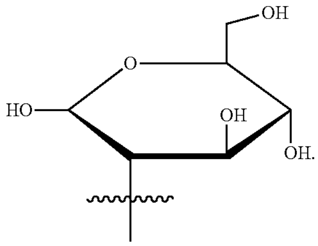

Preferably, the Y is selected from: methyl, ethyl, isopropyl, cyclopropyl, cyclobutyl, cyclohexyl, benzyl,

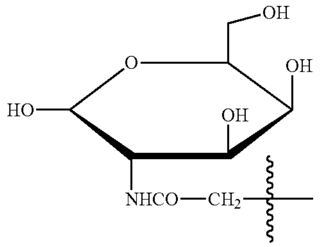

and

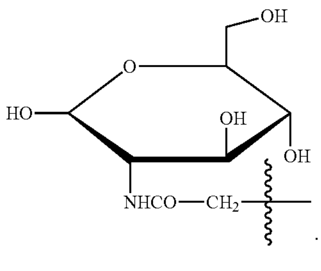

In one preferred embodiment of the present invention, the Y is methyl.

In another preferred embodiment of the present invention, the Y is

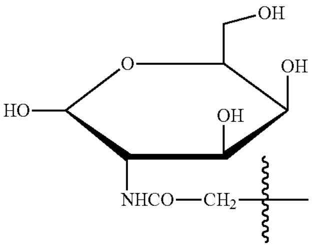

or

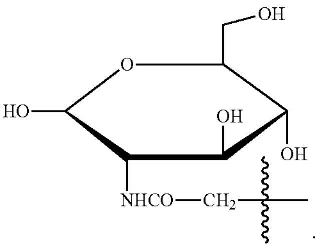

.

In a specific implementation of the present invention, the PEG is a Y-type polyethylene glycol residue and has a structure as shown in a general formula IV or V:

(IV)

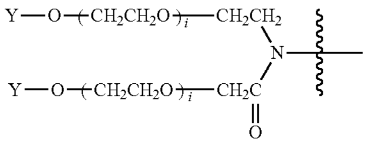

(V)

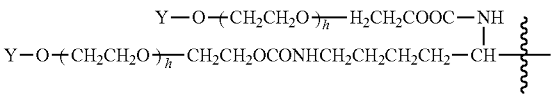

wherein i and h are independently selected from integers in the range of 1-1140, preferably integers in the range of 110-570.

Y has a same definition as in the foregoing general formula II and is preferably selected from: methyl, ethyl, isopropyl, cyclopropyl, cyclobutyl, cyclohexyl, benzyl,

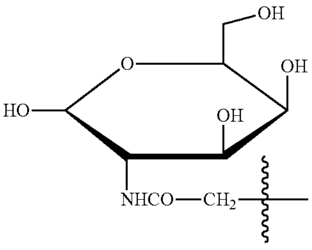

and

-continued

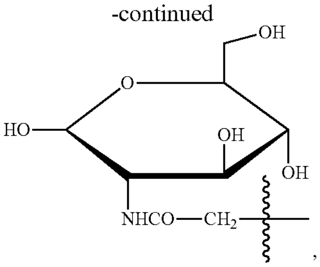

, more preferably selected from: methyl,

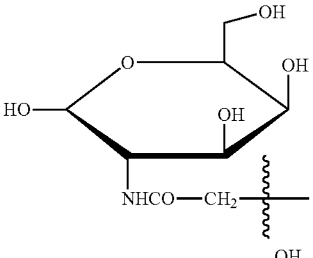

and

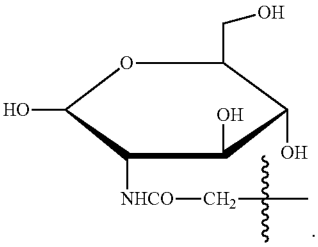

.

In a specific implementation of the present invention, the PEG is a multi-branch polyethylene glycol residue and has a structure as shown in a general formula VI:

(VI)

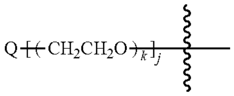

wherein k is an integer in the range of 1-760, preferably an integer in the range of 70-380.

j is an integer in the range of 3-8.

Q is a core molecule of multi-branch polyethylene glycol. Q is selected from: pentaerythritol, oligomerized pentaerythritol, methyl glucoside, sucrose, diethylene glycol, propylene glygol, glycerol and polyglycerol residues, and preferably selected from: pentaerythritol, dipentaerythritol and tripentaerythritol.

Preferably, the multi-branch polyethylene glycol residue has a following structure:

(VII)

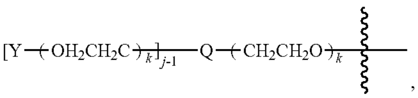

, wherein Q, k and j have same definitions as in the foregoing general formula VI, and Y has a same definition as in the foregoing general formula II and is preferably selected from: methyl, ethyl, isopropyl, cyclopropyl, cyclobutyl, cyclohexyl, benzyl,

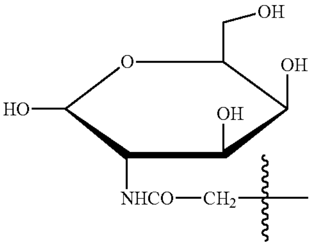

and

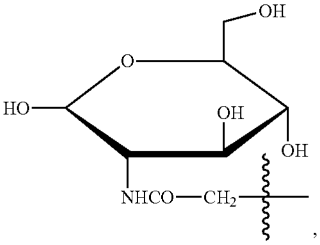

, more preferably selected from: methyl,

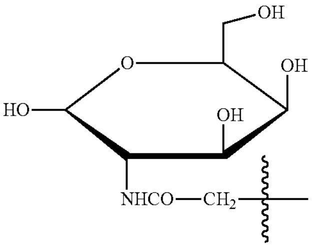

and

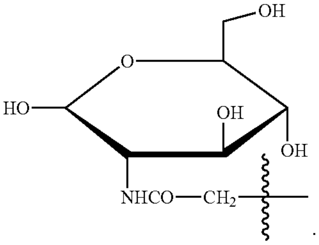

.

In one preferred embodiment of the present invention, the multi-branch polyethylene glycol residue has a following structure:

(VIII)

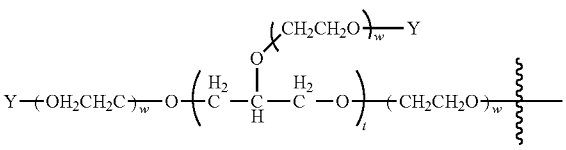

wherein w is an integer in the range of 1-570, preferably an integer in the range of 55-285;

t is an integer in the range of 1-10 (e.g., 1, 2, 3, 4, 5, 6, 7, 8, 9 or 10), preferably an integer in the range of 1-6; and wherein, Y has a same definition as in the foregoing general formula II and is preferably selected from: methyl, ethyl, isopropyl, cyclopropyl, cyclobutyl, cyclohexyl, benzyl,

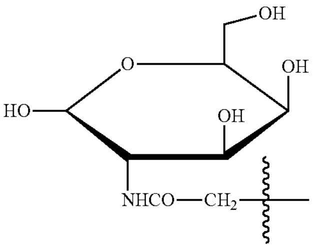

and

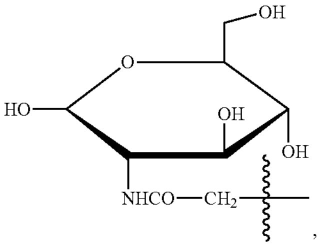

, more preferably selected from: methyl,

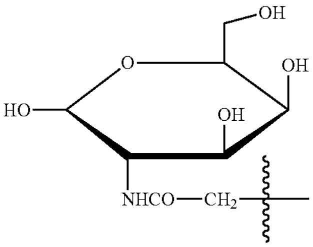

and

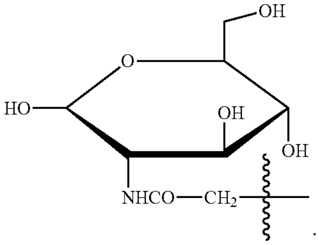

.

In another preferred embodiment of the present invention, the multi-branch polyethylene glycol residue has a following structure:

(IX)

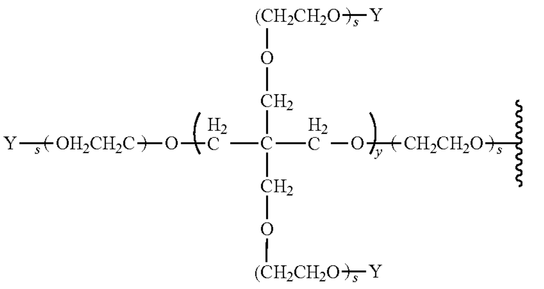

wherein s is an integer in the range of 1-280, preferably an integer in the range of 28-140.

y is an integer in the range of 1-10 (specifically, 1, 2, 3, 4, 5, 6, 7, 8, 9 or 10), preferably an integer in the range of 1-5, more preferably an integer in the range of 1-3.

Y has a same definition as in the foregoing general formula II and is preferably selected from: methyl, ethyl, isopropyl, cyclopropyl, cyclobutyl, cyclohexyl, benzyl,

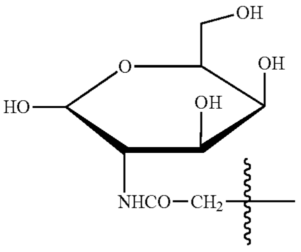

and

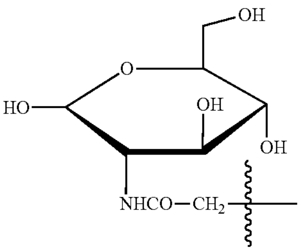

, more preferably selected from: methyl,

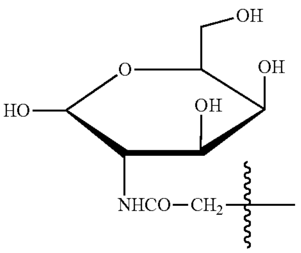

and

-continued

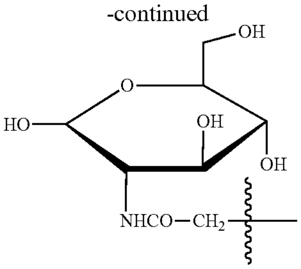

.

A method of separating the blocker from the biomolecule in the step (3) includes: one or a combination of two or more of centrifugal separation, precipitation separation, filtering separation, foam separation, extraction separation, membrane separation, chromatographic separation, electrophoretic separation, and gradient elution.

Provided is a PEGylated biomolecule having controllable binding sites prepared by the above method.

Provided is a pharmaceutical composition prepared from the PEGylated biomolecules having controllable binding sites prepared by the above method and a pharmaceutically acceptable carrier.

Provided is application of the pharmaceutical composition prepared from the PEGylated biomolecules having controllable binding sites prepared by the above method and the pharmaceutically acceptable carrier to preparation of drugs for treating and/or preventing diseases.

In one preferred embodiment of the present invention, the biomolecule is IL-2, and the blocker is an IL-2α receptor (IL-2R α).

In particular, the invention provides a method for preparing PEGylated IL-2 having controllable binding sites, including the following steps:

(1) binding IL-2 to an IL-2α receptor;

(2) PEGylating, coupling PEG with the IL-2; and (3) separating the IL-2 from the IL-2α receptor.

Preferably, the invention provides a method for preparing PEGylated IL-2 having controllable binding sites, including the following steps:

(1) preparing an IL-2α receptor affinity column;

(2) binding IL-2 to an IL-2α receptor on the affinity column;

(3) PEGylating, coupling PEG with the IL-2; and (4) separating the IL-2 from the IL-2α receptor by gradient elution.

The PEGylated IL-2 having controllable binding sites prepared by the above method has a following structure:

$$(PEG—X)_n—IL\text{-}2 \quad (X)$$

n is 1 or 2, and preferably n is 1.

X and PEG have same definitions as preceding definitions. X is a linking group between the PEG and IL-2 and is selected from: a combination of one or more of $—(CH_2)a-$, $—(CR_1R_2)a-$, $—(CH_2)aNH—$, $—NHCO(CH_2)a-$, $—(CH_2)aCONH—$, $—(CH_2)aCO—$, $—CO(CH_2)a-$, $—(CH_2)aCONH(CH_2)a-$, $—(CH_2)a-S—S—(CH_2)a-$, $—(CH_2)aCOO(CH_2)a-$ and $—(CH_2)a-S—(CH_2)a-$.

a is an integer in the range of 0-10. Preferably, the a is an integer in the range of 0-5 (e.g., 0, 1, 2, 3, 4 or 5). More preferably, the a is an integer in the range of 0-3.

$R_1$ and $R_2$ are independently selected from: a combination of one or more of —H, $C_{1-6}$ alkyl, —OR', —NHR', —$N(R')_2$, —CN, —F, —Cl, —Br, —I, —COR', —COOR', —CONHR' or —$CON(R')_2$. Preferably, $R_1$ and $R_2$ are independently selected from: a combination of one or more of H, $C_{1-3}$ alkyl (specifically, methyl, ethyl, n-propyl or isopropyl), —OH, $C_{1-3}$ alkoxy, —$NH_2$, —F, —Cl, —Br and —I. More preferably, $R_1$ and $R_2$ are selected from: H, —$CH_3$, —OH, —$OCH_3$ and —$OCH_2CH_3$. In one embodiment of the present invention, $R_1$ is —H, and $R_2$ is selected from: —$CH_3$, —OH, —$OCH_3$ and —$OCH_2CH_3$.

R is selected from: —H, $C_{1-6}$ alkyl, —F, —Cl, —Br or —I. Preferably, R is selected from: —H and $C_{1-3}$ alkyl (specifically, methyl, ethyl, n-propyl or isopropyl).

Preferably, the X is selected from: a combination of one or more of —$CH_2$—, —$CH_2CH_2$—, —$CH_2CH_2CH_2$—, —$CH_2CONHCH_2$—, —$CH_2CONHCH_2CH_2$—, —$CH_2CONHCH_2CH_2NH$—, —$CH_2CH_2CONHCH_2$—, —$CH_2CO$—, —$CH_2CH_2CO$—, —$CH_2CH_2CONHCH_2CH_2$—, —$CH_2NH$—, —$CH_2CONH$—, —$COCH_2$—, —$COCH_2CH_2$—, —$COCH_2CH_2CH_2$—, —$CH_2COOCH_2$— and —$CH_2$—S—$CH_2$—.

More preferably, the X is selected from: —$CH_2$—, —$CH_2CH_2$—, —$CH_2CH_2CONHCH_2$—, —$CH_2CH_2CO$— and —$CH_2COOCH_2$—.

The PEG is a linear, Y-type and multi-branch polyethylene glycol residue, for example including monomethoxy-polyethylene glycol (mPEG), linear double-terminated PEG, Y-type PEG, 4-arm branched PEG, 6-arm branched PEG or 8-arm branched PEG, etc.

Preferably, a molecular weight of the PEG is in the range of 1-100 KDa, e.g., 1-10 KDa (specifically, 1, 2, 3, 4, 5, 6, 7, 8, 9 or 10 KDa), 10-50 KDa (specifically, 10, 15, 20, 25, 30, 35, 40, 45 or 50 KDa) or 50-100 KDa (specifically, 50, 55, 60, 65, 70, 75, 80, 85, 90, 95 or 100 KDa), etc. Further preferably, the molecular weight of the PEG is in the range of 10-50 KDa.

In a specific implementation of the present invention, the PEG is a linear polyethylene glycol residue and has a structure as shown in a general formula II or III:

(II)

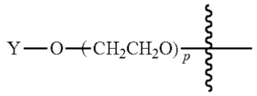

(III)

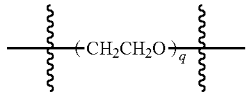

wherein p and q are independently selected from integers in the range of 1-2280, and preferably selected from integers in the range of 220-1140, Y is a capping group and is selected from: H, $C_{1-6}$ alkyl (specifically, methyl, ethyl, n-propyl, isopropyl, n-butyl, isobutyl, tert-butyl, n-pentyl, n-hexyl, etc.), $C_{3-6}$ cycloalkyl (specifically, cyclopropyl, cyclobutyl, cyclopentyl, cyclohexyl, etc.), $C_{6-10}$ aryl (specifically, phenyl, naphthyl, etc.) and -L-T, and L is a linking group between oxygen (O) and a terminal group T and is selected from: a combination of one or more of —$(CH_2)_b$—, —$(CR_3R_4)_b$—, —$(CH_2)_bNH$—, —$NHCO(CH_2)_b$—, —$(CH_2)_bCONH$— and —CO$(CH_2)_b$—, and b is an integer in the range of 0-10.

$R_3$ and $R_4$ are independently selected from: a combination of one or more of —H, $C_{1-6}$ alkyl, —OR", —NHR", —$N(R")_2$, —CN, —F, —Cl, —Br, —I, —COR', —COOR", —OCOR", —CONHR" and —$CON(R")_2$.

R" is selected from: —H, $C_{1-6}$ alkyl, —F, —Cl, —Br and —I.

Preferably, L is selected from: a combination of one or more of —$CH_2$—, —$CH_2CH_2$—, —$CH_2CH_2CH_2$—, —CONH—, —NH—, —CO—, —$CONHCH_2$—, —$CH_2NH$—, —$CH_2CONH$— and —$COCH_2$—.

T is a terminal group and is selected from: H, $C_{1-6}$ alkyl, $C_{3-6}$ cycloalkyl, $C_{6-10}$ aryl, monosaccharide (specifically, glucose, fructose, galactose, ribose, deoxyribose, etc.), and oligosaccharide (specifically, residues of disaccharides including sucrose, lactose, etc. and trisaccharides including gentianose, raffinose, etc.).

Preferably, the T is selected from: methyl, ethyl, isopropyl, cyclopropyl, cyclobutyl, cyclohexyl, benzyl,

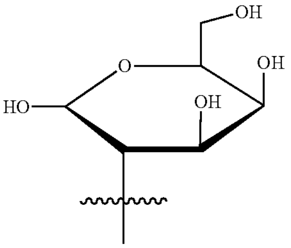

and

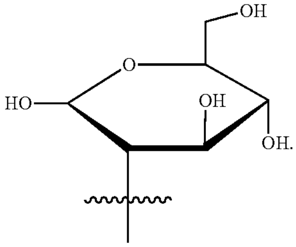

Preferably, the Y is selected from: methyl, ethyl, isopropyl, cyclopropyl, cyclobutyl, cyclohexyl, benzyl,

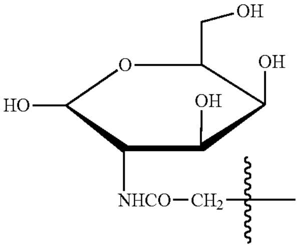

and

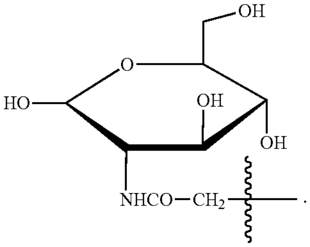

In one preferred embodiment of the present invention, the Y is methyl.

In another preferred embodiment of the present invention, the Y is

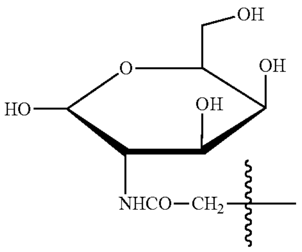

and

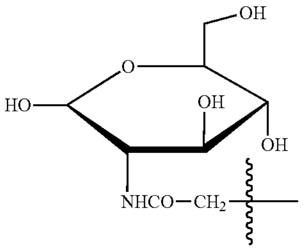

.

In a specific implementation of the present invention, the PEG is a Y-type polyethylene glycol residue and has a structure as shown in a general formula IV or V:

(IV)

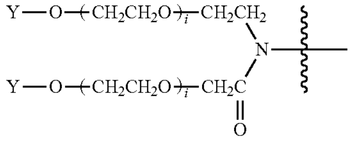

(V)

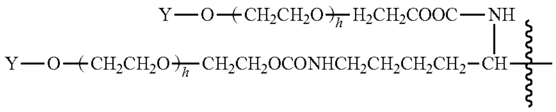

wherein i and h are independently selected from integers in the range of 1-1140, preferably integers in the range of 110-570.

Y has a same definition as in the foregoing general formula II and is preferably selected from: methyl, ethyl, isopropyl, cyclopropyl, cyclobutyl, cyclohexyl, benzyl,

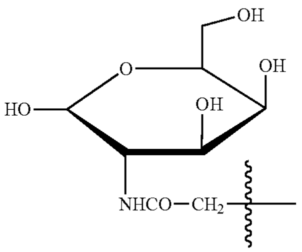

and

-continued

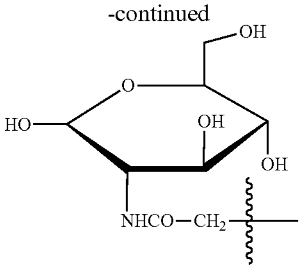

, more preferably selected from: methyl,

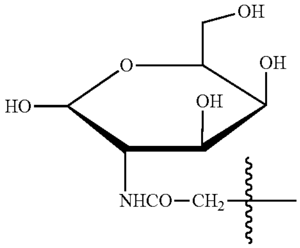

and

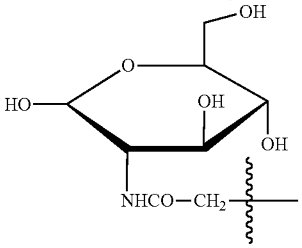

.

In a specific implementation of the present invention, the PEG is a multi-branch polyethylene glycol residue and has a structure as shown in a general formula VI:

(VI)

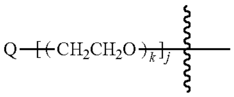

wherein k is an integer in the range of 1-760, preferably an integer in the range of 70-380.

j is an integer in the range of 3-8.

Q is a core molecule of multi-branch polyethylene glycol. Q is selected from: pentaerythritol, oligomerized pentaerythritol, methyl glucoside, sucrose, diethylene glycol, propylene glygol, glycerol and polyglycerol residues, and preferably selected from: pentaerythritol, dipentaerythritol and tripentaerythritol.

Preferably, the multi-branch polyethylene glycol residue has a following structure:

(VII)

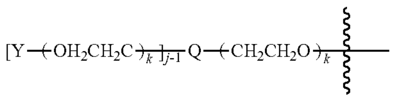

wherein Q, k and j have same definitions as in the foregoing general formula VI, and Y has a same definition as in the foregoing general formula II and is preferably selected from: methyl, ethyl, isopropyl, cyclopropyl, cyclobutyl, cyclohexyl, benzyl,

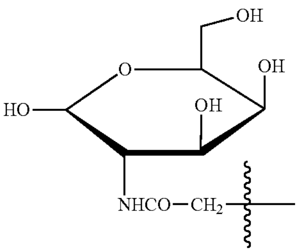

and

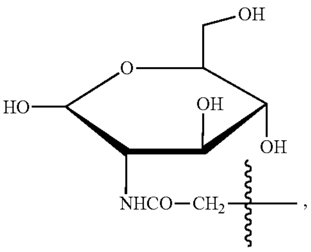

more preferably selected from: methyl,

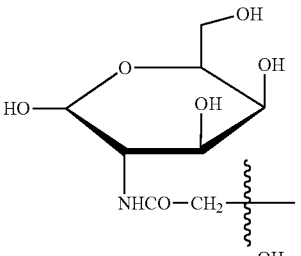

and

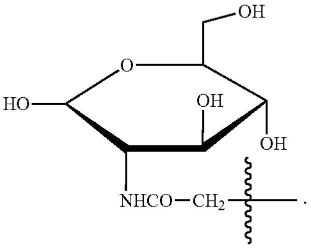

In one preferred embodiment of the present invention, the multi-branch polyethylene glycol residue has a following structure:

(VIII)

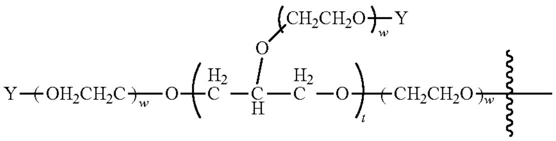

wherein w is an integer in the range of 1-570, preferably an integer in the range of 55-285, t is an integer in the range of 1-10 (e.g., 1, 2, 3, 4, 5, 6, 7, 8, 9 or 10), preferably an integer in the range of 1-6, and wherein, Y has a same definition as in the foregoing general formula II and is preferably selected from: methyl, ethyl, isopropyl, cyclopropyl, cyclobutyl, cyclohexyl, benzyl,

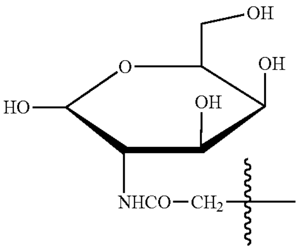

and

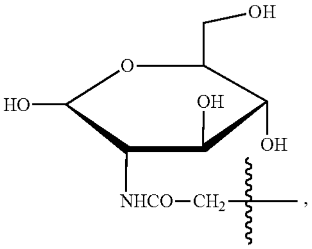

more preferably selected from: methyl,

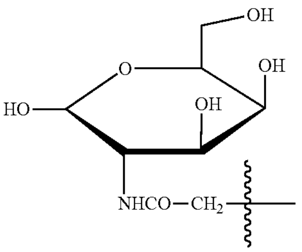

and

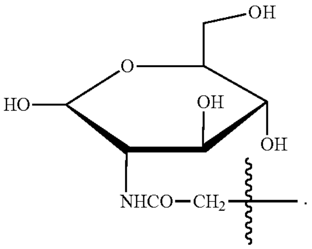

In another preferred embodiment of the present invention, the multi-branch polyethylene glycol residue has a following structure:

(IX)

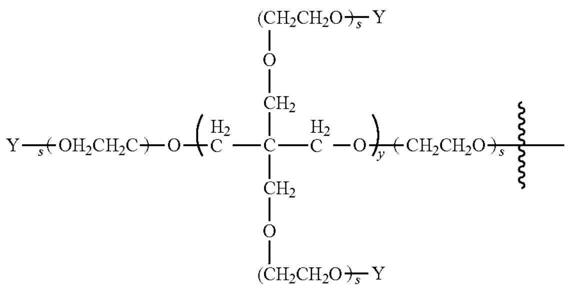

wherein s is an integer in the range of 1-280, preferably an integer in the range of 28-140.

y is an integer in the range of 1-10 (specifically, 1, 2, 3, 4, 5, 6, 7, 8, 9 or 10), preferably an integer in the range of 1-5, more preferably an integer in the range of 1-3.

Y has a same definition as in the foregoing general formula II and is preferably selected from: methyl, ethyl, isopropyl, cyclopropyl, cyclobutyl, cyclohexyl, benzyl,

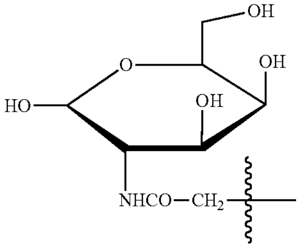

and

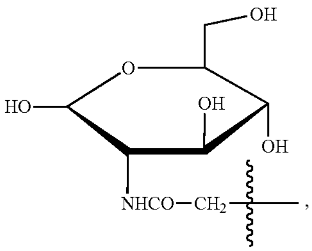

, more preferably selected from: methyl,

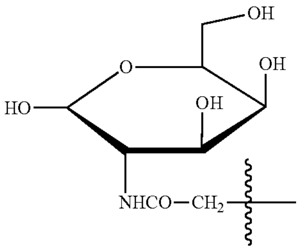

and

-continued

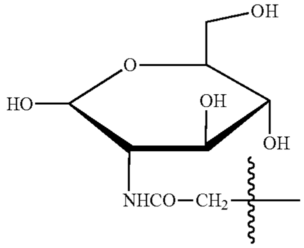

.

Provided is a pharmaceutical composition prepared from the PEGylated IL-2 having controllable binding sites prepared by the above method and a pharmaceutically acceptable carrier.

Provided is application of the pharmaceutical composition prepared from the PEGylated IL-2 having controllable binding sites prepared by the above method and the pharmaceutically acceptable carrier to preparation of drugs for treating and/or preventing diseases.

Preferably, the diseases are tumors, autoimmune diseases, viral diseases, or bacterial diseases.

The tumor diseases include renal cell carcinoma, melanoma, malignant hemangioendothelioma, cutaneous T cell tumor, ovarian cancer, breast cancer, bladder cancer, lung cancer, glioma, neuroblastoma, liver cancer, hairy cell leukemia, myeloid blast cell leukemia, colon cancer, cancerous pleural effusion, or non-Hodgkin's lymphoma.

The autoimmune diseases include rheumatoid arthritis, systemic lupus erythematosus or sicca syndrome.

Viruses include hepatitis virus, papilloma virus, herpes simplex virus (HSV), human immunodeficiency virus (HIV), Epstein-Barr virus (EBv), coronavirus and influenza virus, more preferably hepatitis virus such as hepatitis B virus (HBV) or hepatitis C virus (HCV).

The bacterial diseases include leprosy or tuberculosis.

Unless defined otherwise, all technical and scientific terms as used in the present invention have the same meanings as those usually understood by those skilled in the field of the present invention, for example:

the terms "Interleukin 2", "interleukin 2" and "IL-2" have the same meaning and are used interchangeably herein, may be nature interleukin 2, a recombinant protein (e.g., recombinant human interleukin 2), or a mutant that also has a nature IL-2 function (e.g., "IL-2-C125A/L18M/L19S" as described in the doctoral dissertation "Recombinant Human Interleukin-2 (IL-2) Mutant Cloning and Expression and Purification in *Pichia Pastoris* System" by LIU Yan), and may also include products obtained by tissue culture, protein synthesis, and cell culture (nature, recombinant cells or mutant) methods. Methods for the extraction and separation of nature, recombinant IL-2 or mutant are well known to those skilled in the art.

As used herein, the term "pharmaceutically acceptable" means physiologically compatible upon administration to a human and does not cause gastrointestinal disorders, such as allergic reactions or similar reactions like dizziness. Additives can be any one of excipients, disintegrants, binders, lubricants, suspending agents, stabilizers, etc. Examples of the excipients include lactose, mannitol, isomalt, microcrystalline cellulose, siliconized microcrystalline cellulose, powdered cellulose, etc. Examples of the disintegrants include low substituted hydroxypropyl cellulose, crospovidone, sodium starch glycolate, croscarmellose sodium, starch, etc. Examples of the binders include hydroxypropyl cellulose, hypromellose, povidone, copovidone, pregelatinized starch, etc. Examples of the lubricants include stearic acid, magnesium stearate, sodium fumaryl stearate, etc. Examples of wetting agents include polyoxyethylene sorbitan fatty acid ester, poloxamer, polyoxyethylene castor oil derivatives, etc. Examples of the suspending agents include hypromellose, hydroxypropyl cellulose, povidone, copovidone, sodium carboxymethylcellulose, methylcellulose, etc. Examples of the stabilizers include citric acid, fumaric acid, succinic acid, etc. In addition, the pharmaceutical composition of the present invention may further include any one of a retarder, a flavoring agent, an emulsifier, a preservative, etc.

The pharmaceutical composition of the present invention may be in the form of tablets (including sugar-coated tablets, film-coated tablets, sublingual tablets, orally disintegrating tablets, buccal tablets, etc.), pills, powder, granules, capsules (including soft capsules, and microcapsules), lozenges, syrups, liquid, emulsions, suspensions, controlled release preparations (e.g., instantaneous release preparations, sustained release preparations, and sustained release microcapsules), aerosol, films (e.g., orally disintegrating films, and oral muco-adhesive films), injections (e.g., subcutaneous injections, intravenous injections, intramuscular injections, and intraperitoneal injections), intravenous dripping agents, transdermal absorption preparations, ointments, lotions, adhesive preparations, suppositories (e.g., rectal suppositories, and vaginal suppositories), pellets, nasal preparations, pulmonary preparations (inhalants), ocular drops, etc., and oral or parenteral preparations (e.g., administration forms of intravenous, intramuscular, subcutaneous, intraorgan, intranasal, intradermal, drip, intracerebral, intrarectal, etc., administration to the vicinity of a tumor and direct administration to a lesion). Preferably, the pharmaceutical composition is an injection.

Preferably, a pharmaceutically acceptable adjuvant of the present invention is preferably a pharmaceutically acceptable injection adjuvant, e.g., an isotonic sterile saline solution (sodium dihydrogen phosphate, disodium hydrogen phosphate, sodium chloride, potassium chloride, calcium chloride, magnesium chloride, etc., or a mixture of the foregoing salts), or a dry, e.g., freeze-dried, composition which is suitably formed into an injectable solute by the addition of sterile water or physiological saline.

The PEGylated IL-2 of the present invention may be abbreviated PEG-IL-2.

DETAILED DESCRIPTION

Figure 1:
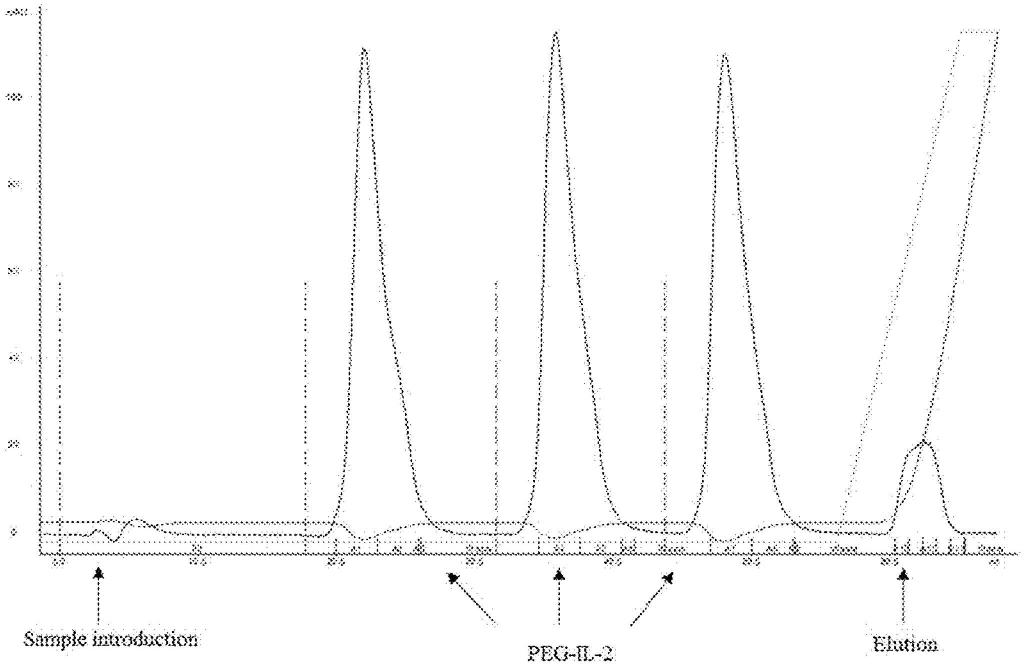
FIG. 1 is a chromatograph of PEGylation of IL-2 on a receptor affinity column.
Figure 2:
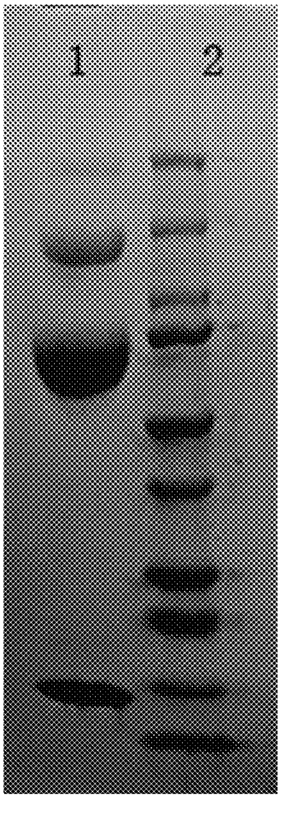
FIG. 2 shows an electrophoresis result of PEG-IL-2, wherein 1 represents the PEG-IL-2 and 2 represents a marker.

The technical solutions in the embodiments of the present invention will be clearly and completely described below. It is obvious that the described embodiments are only a part of embodiments of the present invention, but not all embodiments of the present invention. All the other embodiments obtained by those of ordinary skill in the art based on the embodiments of the present invention without any creative efforts all belong to the protection scope of the present invention.

Embodiment 1 Preparation of IL-2α Receptor Affinity Column

S1: 0.8 g of CNBr activated sepharose (sepharose CNBr) was weighed, and added into 12 ml of 1 mM HCl, manually and slowly mixed well, and put into a refrigerator at 4° C. to be subjected to a reaction for 15 min;

S2: A coupling buffer was prepared: 0.1 M $NaHCO_3$ (pH=8.3) and 0.5 M NaCl were well mixed, and 12 ml of coupling buffer was taken to wash a filler swollen in the last step;

S3: Four bottles, 4 mg in total, of IL-2α receptor was taken, dissolved in 2 ml of coupling buffer, and added to the filler swollen in the step 2;

S4: Slow rocking-turn was conducted at room temperature for 2 h;

S5: An excess receptor was washed away with 5 column volumes of coupling buffer;

S6: 0.1 M tris(hydroxymethyl)aminomethane (Tris-HCl) (pH=8.0) was added, the mixture was placed at room temperature for 2 h, and the Tris-HCl was poured away;

S7: Washing was conducted with 5 column volumes of 0.1 M acetic acid/sodium acetate buffer (pH=4.0) containing 0.5 M NaCl, and then washing was conducted with 5 column volumes of 0.1 M Tris-HCl buffer (pH=8.0) containing 0.5 M NaCl;

S8: The step 6 and step 7 were repeated for three times;

S9: 0.5 ml of 0.1 M Tris-HCl (pH=8.0) was added; and

S10: A 5 ml empty column was filled with sepharose resin, and preserved in the refrigerator at 4° C.

Embodiment 2 PEGylation of IL-2 on Receptor Affinity Column

S1: A 5 ml receptor affinity column was mounted on a protein purification system (AKTA purifier);

S2: Mobile phases, including a phase A: 5 mM PBS (pH=7.0), and a phase B: a 0.2 M acetic acid solution containing 0.2 M NaCl, were prepared;

S3: A mobile phase flow rate was set to be 0.45 ml/min;

S4: The phase A was balanced to a stable UV curve;

S5: An IL-2 sample was fed through a sampling loop, and an a receptor binding site on IL-2 was bound to an IL-2α receptor;

S6: A proper amount of methoxyl polyethylene glycol-succinimide propionate (M-SPA-20K) with a molecular weight of 20 KDa was taken, and dissolved in 2.5 mM PB (pH=8.0) to a final concentration of 40 mg/ml, 2 ml of M-SPA-20K was sucked, and fed through a sampling loop, and balanced to a stable UV curve;

S7: The step 6 was repeated for three times; and

S8: Gradient elution was conducted, a chromatograph was as shown in FIG. 1, elution peaks were collected, ultrafiltrated, concentrated, and detected by sodium dodecylsulfate-polyacrylamide gel electrophoresis (SDS-PAGE).

Embodiment 3 Gel Filtration Chromatographic Separation of PEG-IL-2

Gel filtration chromatography settings include: a mobile phase: 5 mM PBS, a flow rate: 0.75 ml/min, and a column: superdex 200 increase 10/300 GL.

Figure 3:
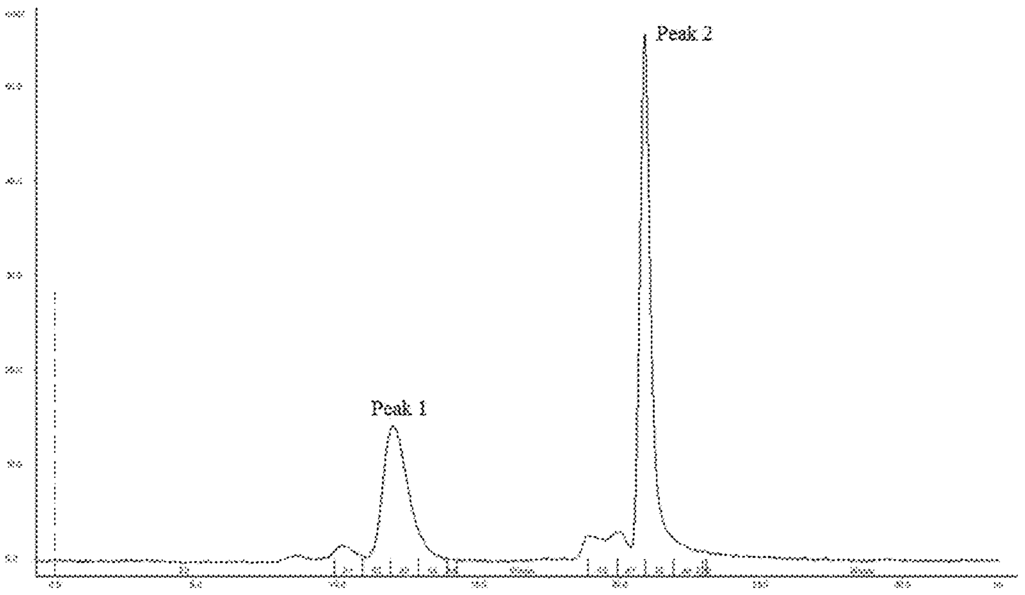
FIG. 3 is a chromatograph of gel chromatographic separation of PEG-IL-2.

Separation includes: S1: a chromatographic system was balanced to a stable UV curve; S2: elution peaks were collected after sampling; and S3: the collected components were ultrafiltrated, concentrated, and detected by SDS-PAGE, and results were as shown in FIG. 3 and FIG. 4.

Figure 4:
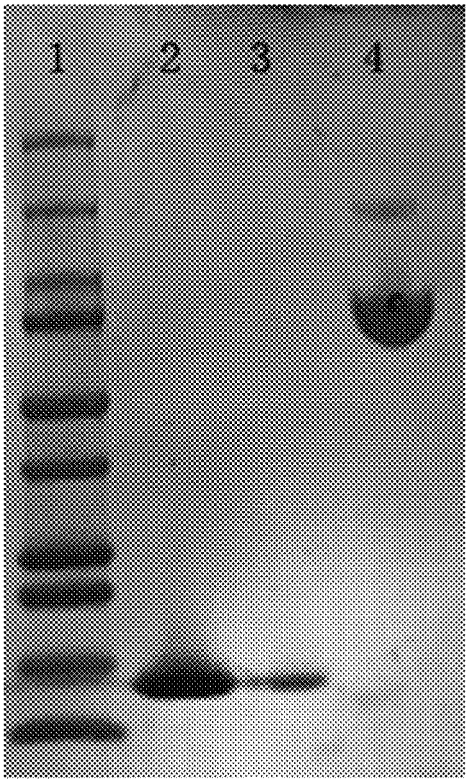
FIG. 4 shows an SDS-PAGE result of PEG-IL-2, wherein 1 represents a marker, 2 represents IL-2, 3 represents a peak 2, and 4 represents a peak 1.

Detection results: after confirmation by SDS-PAGE, in FIG. 4, a peak 1 represents PEG-IL-2 and a peak 2 represents IL-2.

Embodiment 4 Test on Receptor Affinities

Samples at the peak 1 (PEG-IL-2) and the peak 2 (IL-2) in FIG. 4 were collected, respectively. Test on affinities was carried out by an SPR instrument after concentration. Receptor proteins included an IL-2α receptor and an IL-2β receptor. Test results were as below:

TABLE 1

| Sample | PEG-IL-2 | IL-2 |
|---|---|---|
| IL-2/IL-2Rα (μM) | 0.34 | 0.023 |
| IL-2/IL-2Rβ (μM) | 31.96 | 2.80 |

Results in the above table show that the PEG-IL-2 prepared by the method of the present invention has a relatively strong binding force to the IL-2β receptor.

Finally, it should be noted that the above embodiments are merely used to describe the technical solutions of the present invention, but not intended to limit the present invention. Although the present invention is described in detail with reference to the preceding embodiments, it should be appreciated that those of ordinary skill in the art may still make modifications of the technical solutions described in the preceding embodiments or make equivalent replacements to some or all technical features. Such modifications or replacements do not make the nature of the corresponding technical solutions depart from the scope of the technical solutions of the embodiments of the present invention.

The invention claimed is:

1. A method of preparing PEGylated IL-2 having controllable binding sites, comprising the following steps:

(1) preparing an IL-2α receptor affinity column;

(2) binding IL-2 to an IL-2α receptor on the affinity column;

(3) PEGylating, coupling PEG with the IL-2; and (4) separating the IL-2 from the IL-2α receptor by gradient elution;

wherein the PEGylated IL-2 has the following structure:

$$(\mathrm{PEG}-\mathrm{X})_n-\mathrm{IL\text{-}2}$$

wherein:

n is 2;

X is a linking group between the PEG and IL-2 and is $-(CH_2)aCO-$;

a is 2;

the PEG is a linear monomethoxypolyethylene glycol residue;

a molecular weight of the PEG is in the range of 10-50 KDa;

wherein the PEGylated IL-2 having controllable binding sites selectively binds to an IL-2 βγ-type receptor.

* * * * *